(12) United States Patent
Moriya et al.

(10) Patent No.: US 7,464,581 B2
(45) Date of Patent: Dec. 16, 2008

(54) VACUUM APPARATUS INCLUDING A PARTICLE MONITORING UNIT, PARTICLE MONITORING METHOD AND PROGRAM, AND WINDOW MEMBER FOR USE IN THE PARTICLE MONITORING

(75) Inventors: Tsuyoshi Moriya, Nirasaki (JP); Hiroyuki Nakayama, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 259 days.

(21) Appl. No.: 11/091,417

(22) Filed: Mar. 29, 2005

(65) Prior Publication Data

US 2005/0268694 A1 Dec. 8, 2005

Related U.S. Application Data

(60) Provisional application No. 60/635,617, filed on Dec. 14, 2004.

(30) Foreign Application Priority Data

Mar. 29, 2004 (JP) .............................. 2004-096456
Nov. 12, 2004 (JP) .............................. 2004-329675

(51) Int. Cl.
*G01N 21/47* (2006.01)
*G01N 21/53* (2006.01)

(52) U.S. Cl. ................ 73/28.01; 073/28.08; 073/31.05; 250/573; 250/574; 356/335; 356/336

(58) Field of Classification Search ................ 073/23.2, 073/28.01–28.06, 31.05, 31.07; 250/216, 250/573–577; 356/335–338, 340–343
See application file for complete search history.

(56) References Cited

U.S. PATENT DOCUMENTS 4,466,872 A * 8/1984 Einbinder .............. 204/192.13
5,126,032 A * 6/1992 Szczyrbowski et al. 204/298.08
5,271,264 A * 12/1993 Chanayem ................ 73/28.01

(Continued)

FOREIGN PATENT DOCUMENTS

JP 10284471 A * 10/1998

(Continued)

*Primary Examiner*—David A. Rogers
(74) *Attorney, Agent, or Firm*—Oblon, Spivak, McClelland, Maier & Neustadt, P.C.

(57) ABSTRACT

It is an object to provide a vacuum apparatus capable of evaluating its cleanness precisely by surely monitoring particles including deposits readily detached from the apparatus, and a particle monitoring method and program employed therein, and a window member for particle monitoring.

A semiconductor manufacturing apparatus 1000 includes a processing chamber 100 for performing a manufacturing processing on a wafer. A gas supply line for introducing a purge gas is connected to an upper portion of the processing chamber 100, a valve 120 being installed on the gas supply line. A rough pumping line 200 with a valve a is connected to a lower portion of the processing chamber 100. Installed on the rough pumping line 200 are a dry pump 220 for exhausting a gas in the processing chamber 100 and a particle monitoring unit 210 for monitoring particles between the valve a and the dry pump 220. In the semiconductor manufacturing apparatus 1000, after the valve 120 is opened, the purge gas is supplied to apply physical vibration due to shock wave in the processing chamber 100 so that deposits are detached therefrom to be monitored as particles.

8 Claims, 8 Drawing Sheets

U.S. PATENT DOCUMENTS

| | | | |
|---|---|---|---|
| 5,436,465 A * | 7/1995 | Borden et al. | 250/574 |
| 5,837,094 A * | 11/1998 | Tsukazaki et al. | 156/345.25 |
| 5,943,130 A * | 8/1999 | Bonin et al. | 356/336 |
| 6,216,548 B1 * | 4/2001 | Park et al. | 73/863.02 |
| 6,576,559 B2 * | 6/2003 | Nakata et al. | 438/706 |
| 6,696,362 B2 * | 2/2004 | Rossman et al. | 438/680 |
| 6,737,666 B1 * | 5/2004 | Ito et al. | 250/574 |
| 6,755,934 B2 * | 6/2004 | Matsuoka | 156/345.33 |
| 6,797,110 B2 * | 9/2004 | Takano et al. | 156/345.41 |
| 6,815,653 B2 * | 11/2004 | Tsay et al. | 250/206 |
| 6,878,214 B2 * | 4/2005 | Murugesh et al. | 134/18 |
| 2003/0054655 A1 * | 3/2003 | Nakano et al. | 438/710 |
| 2003/0147075 A1 * | 8/2003 | Otsuki et al. | 356/338 |

FOREIGN PATENT DOCUMENTS

| | | | |
|---|---|---|---|
| JP | 2000091247 A | * | 3/2000 |

* cited by examiner

VACUUM APPARATUS INCLUDING A PARTICLE MONITORING UNIT, PARTICLE MONITORING METHOD AND PROGRAM, AND WINDOW MEMBER FOR USE IN THE PARTICLE MONITORING

FIELD OF THE INVENTION

The present invention relates to a vacuum apparatus including a particle monitoring unit, a particle monitoring method and a program therefor, and a window member for use in the particle monitoring.

BACKGROUND OF THE INVENTION

A semiconductor manufacturing apparatus (FIG. 10) using plasma is employed to perform, for example, an etching processing on a semiconductor wafer (hereinafter, referred to as "wafer") in the course of manufacturing semiconductor products. If particles generated during a manufacturing processing adhere to product wafers, the wafers would be contaminated, resulting in reduction in yield. Thus, a high level of cleanness is required for the semiconductor manufacturing apparatus.

Figure 10:
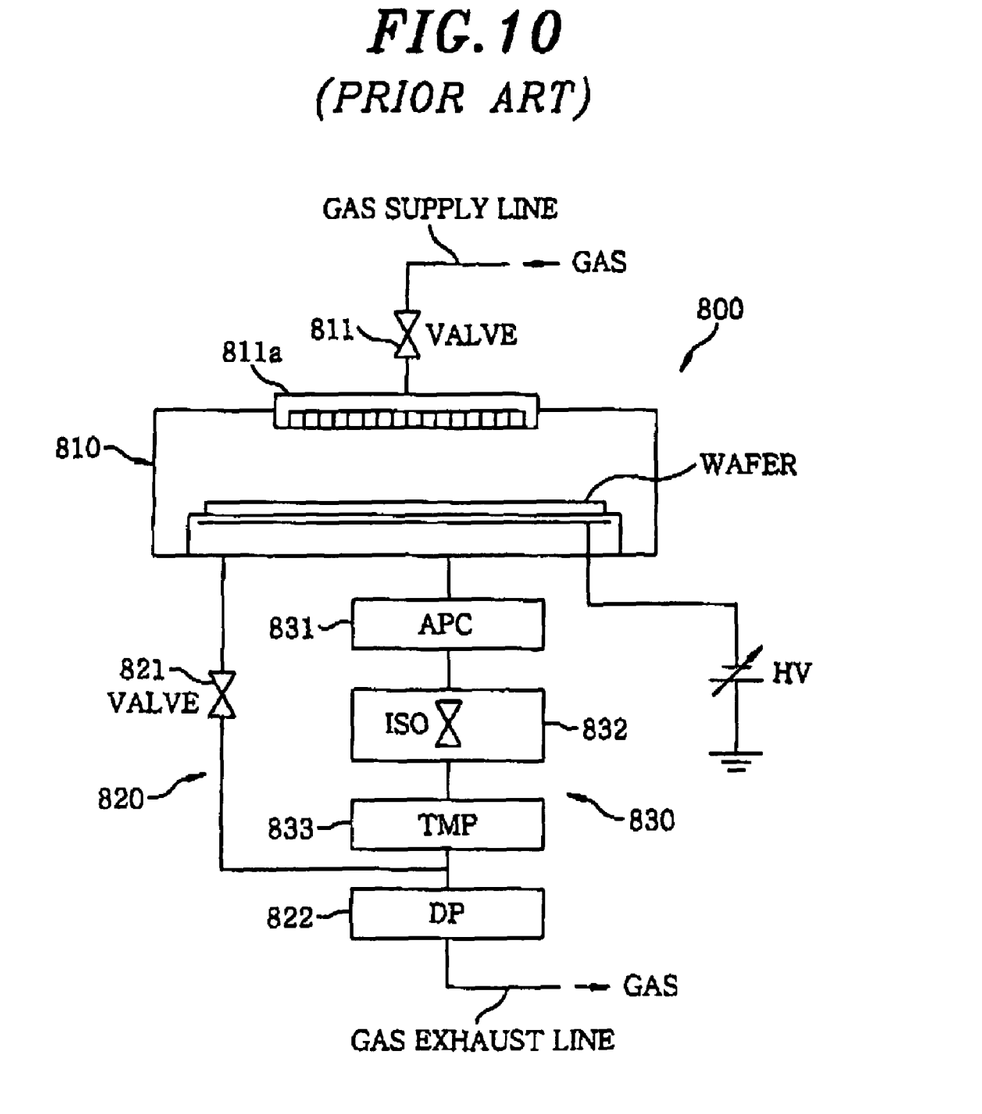
FIG. 10 is a schematic configuration view of a conventional semiconductor manufacturing apparatus.

FIG. 10 illustrates a schematic configuration view of a conventional semiconductor manufacturing apparatus 800.

In FIG. 10, the semiconductor manufacturing apparatus 800 includes a processing chamber 810 formed of a cylindrical vessel for performing various processings on a wafer. The processing chamber 810 houses therein a wafer stage for mounting a wafer thereon, and an electrode to which a high voltage is to be applied is buried in the wafer stage. Further, a shower head 811a provided with a number of through holes is disposed at an upper portion of the processing chamber 810, and the shower head 811a serves to introduce an corrosive processing gas for use in a manufacturing processing into the processing chamber 810 via the through holes.

Moreover, a gas supply line formed of a tubular member is connected to the upper portion of the processing chamber 810 to introduce a purge gas into the processing chamber 810. A valve 811 for controlling the flow rate of the purge gas is installed on the gas supply line. Further, a rough pumping line 820 formed of a thin tubular member and a main vacuum pumping line 830 formed of a thick tubular member are coupled to lower portions of the processing chamber 810. The rough pumping line 820 and the main vacuum pumping line 830 are merged into a gas exhaust line.

Installed on the rough pumping line 820 are a dry pump (DP) 822 for exhausting a gas from the processing chamber 810 via the gas exhaust line and a valve 821 for controlling the flow rate of the gas exhausted by the dry pump 822.

Further, on the main vacuum pumping line 830, an automatic pressure controller (APC) 831, an isolation valve (ISO) 832 serving as a gate valve and a turbo molecular pump (TMP) 833 having a gas pumping rate greater than that of the dry pump 822 are installed in that order from the side of the processing chamber 810.

In case of depressurizing the processing chamber 810 of the semiconductor manufacturing apparatus 800 for the manufacturing processing, the processing chamber 810 is first evacuated via the rough pumping line 820 and then, after closing the valve 821, the processing chamber 810 is regulated at a desired vacuum level by means of the main vacuum pumping line 830. When performing an etching processing during the manufacturing process, a high vacuum state is required, and, to maintain the high vacuum level, the vacuum pumping via the main vacuum pumping line 830 is continued during the manufacturing process.

After the completion of the manufacturing processing, a purge gas is supplied into the processing chamber 810 via the gas supply line and is then exhausted externally via the gas exhaust line, during which particles floating within the processing chamber 810 are removed from the processing chamber 810 along with the purge gas, so that the processing chamber 810 is cleaned (see, for example, Japanese Patent Laid-open Application No. H6-056999: Reference 1).

To evaluate the cleanness of the processing chamber 810, there have been made various attempts to monitor particles by using an optical particle monitoring unit (PM)(not shown) which is on the market.

The particle monitoring unit is usually installed between the automatic pressure controller 831 on the main vacuum pumping line 830 and the processing chamber 810, between the automatic pressure controller 831 and the isolation valve 832, or inside the processing chamber 810 to monitor particles discharged from the chamber 810 in real time during the manufacturing processing.

As for the particle monitoring unit, its component, for example, a lens formed of glass tends to be readily corroded by a corrosive processing gas. For example, glass components of the particle monitoring unit would be whitened in about a week after they are first used. Accordingly, the whitened components need to be replaced by new ones or be subject to maintenance work. Consequently, costs of the semiconductor manufacturing apparatus 800 are increased, while its operating time decreases. As a solution to this problem, by installing the particle monitoring unit on the rough pumping line 820, it is possible to prevent the corrosion of the glass components of the particle monitoring unit.

Since it is difficult to monitor the particles that are moving at a high speed of, for example, 20 m/sec, there has been proposed a technique for allowing the particle monitoring unit to monitor the particles by controlling the flow cross-sectional area of a gas that flows through the gas exhaust line such as the vacuum main pumping line 830 formed of a thick tubular member, to thereby improve the probability for detecting the particles (see, for example, Japanese Patent Laid-open Application No. H11-304688: Reference 2).

Further, the semiconductor manufacturing apparatus 800 in FIG. 10 further includes a transparent window member (not shown) formed of quartz glass ($SiO_2$). The window member is installed to face the processing chamber 810 and serves as a window for introducing, for example, a microwave into the processing chamber 810.

If the quartz glass forming the window member is exposed to fluorine-based plasma atmosphere, the silicon (Si) atom of $SiO_2$ would react with an active molecule such as a fluorine radical contained in the fluorine-based plasma and then volatilize as silicon fluoride ($SiF_4$), thereby contaminating the wafer or depositing on the surface of the window member to blur it (i.e., deterioration occurs).

Typically, for the purpose of preventing such deterioration, the quartz glass is heated. Further, to suppress the deterioration of the window member, there has been also proposed a window member formed of a member made by dispersing a first phase of quartz into a second phase of alumina ($Al_2O_3$) (see, for example, U.S. Pat. No. 6,797,110: Reference 3). Furthermore, for parts such as bell jar and a focus ring which are used in the processing chamber other than the window member, there has been an amorphous material of silica and alumina formed by melting silica ($SiO_2$) containing aluminum (Al) (see, for example, Japanese Patent Laid-open Application No. 2003-292337: Reference 4). All of these techniques aim at improving the resistance to the fluorine-based plasma or the active molecules by forming a preset member containing aluminum therein.

However, References 1 and 2 disclose merely the technique of monitoring particles that are moving along with the gas exhausted from the processing chamber 810, but none of them discloses or suggests a technique of monitoring deposits adhered on the inner wall of the processing chamber 810.

The deposits might come apart from the inner wall of the processing chamber 810 during the manufacturing process and the like, resulting in a contamination of the wafer. Therefore, it is required to evaluate the cleanness of the processing chamber 801 more precisely by monitoring the deposits on the chamber wall as well.

In addition, when heating the quartz glass of the window member to prevent the deterioration thereof, a defect may be caused in an electric circuit disposed within the semiconductor manufacturing apparatus 800 or deterioration of a laser unit may be accelerated.

Furthermore, with regard to the above techniques for allowing a member to contain aluminum therein, since aluminum atoms are dispersed in silica or quartz, the surface of the member cannot exhibit plasma resistance or resistance to active molecules efficiently, so that the frequency of replacing the member increases. As a result, the time required for the replacement work increases, which in turn results in deterioration in the productivity of the semiconductor manufacturing apparatus 800. Moreover, due to the increase of costs for the replacements, overall costs of the semiconductor manufacturing apparatus 800 rises. Further, to prevent the deterioration of the productivity of the semiconductor manufacturing apparatus 800 and increase of the costs, the window member for use in the particle monitoring apparatus connected to, for example, the main vacuum pumping line also needs to meet the condition of low frequency of replacement.

SUMMARY OF THE INVENTION

It is, therefore, a first object of the present invention to provide a vacuum apparatus capable of evaluating its cleanness precisely by monitoring particles including deposits readily detached from the apparatus, and a particle monitoring method and program employed therein.

It is a second object of the present invention to provide a window member for particle monitoring which exhibits resistance to active molecules, thus capable of reducing the frequency of its replacement.

In order to achieve the first object, there is provided a vacuum apparatus including: a vessel for defining a predetermined space; a gas exhaust unit for exhausting a gas from the vessel via a gas exhaust line; at least one gas exhaust control unit installed on the gas exhaust line, for controlling a flow rate of the gas exhausted from the vessel; a particle monitoring unit installed on the gas exhaust line between said at least one gas exhaust control unit and the gas exhaust unit, for monitoring particles within the gas exhaust line; a purge unit for supplying a purge gas into the vessel via a gas supply line; and a gas supply control unit installed on the gas supply line between the purge unit and the vessel, for controlling a flow rate of the purge gas supplied into the vessel, wherein the gas supply control unit starts a supply of the purge gas when said at least one gas exhaust control unit permits an exhaust of the gas, and the particles monitored by the particle monitoring unit include the particles detached from the vessel due to the supply of the purge gas.

With the vacuum apparatus, since the particles detached from the vessel due to the supply of the purge gas which starts when the exhaust of the gas is permitted are monitored, it is possible to surely monitor the particle including deposits which readily separate, enabling an accurate evaluation of the cleanness in the vacuum apparatus.

The apparatus may further includes: a processing gas supply unit for supplying a corrosive processing gas into the vessel; and another gas exhaust unit for exhausting the processing gas from the vessel, wherein said at least one gas exhaust control unit prohibits the exhaust of the gas when the processing gas is exhausted by said another gas exhaust unit. In this way, by prohibiting the exhaust of the gas via the exhaust line when the processing gas is exhausted via another exhaust line, the corrosion of the particle monitoring unit can be prevented and the life span thereof can be extended.

It is preferable that the gas supply control unit controls the flow rate of the purge gas such that the pressure value of the purge gas becomes at least twice the internal pressure of the vessel. By controlling the flow rate of the purge gas such that the pressure value of the purge gas becomes at least twice the internal pressure of the vessel, shock wave can be positively generated in the vessel and deposits can be surely detached therefrom.

In order to achieve the first object, there is provided a vacuum apparatus including: a vessel for defining a predetermined space; a gas exhaust unit for exhausting a gas from the vessel via a gas exhaust line; at least one gas exhaust control unit installed on the gas exhaust line, for controlling a flow rate of the gas exhausted from the vessel; a particle monitoring unit installed on the gas exhaust line between said at least one gas exhaust control unit and the gas exhaust unit, for monitoring particles within the gas exhaust line; and a power supply unit for generating an electric discharge within the vessel, wherein the power supply unit starts the electric discharge when said at least one gas exhaust control unit permits the exhaust of the gas, and the particles monitored by the particle monitoring unit include the particles detached from the vessel due to the electric discharge.

With the vacuum apparatus, since the particles detached from the vessel due to the electric discharge which starts when the exhaust of the gas is permitted are monitored, it is possible to surely monitor the particle including deposits which readily separate, enabling an accurate evaluation of the cleanness in the vacuum apparatus.

It is preferable that the power supply unit generates an electromagnetic stress in the vessel due to the electric discharge. In this way, since an electromagnetic stress is generated due to the electric discharge in the vessel, deposits can be positively detached from the vessel.

The apparatus may further includes: a purge unit for supplying a purge gas into the vessel via a gas supply line; and a gas supply control unit installed on the gas supply line between the purge unit and the vessel, for controlling a flow rate of the purge gas supplied into the vessel, wherein the gas supply control unit starts a supply of the purge gas when said at least one gas exhaust control unit permits an exhaust of the gas, and the particles monitored by the particle monitoring unit include the particles detached from the vessel due to the supply of the purge gas. With the apparatus, since there are monitored the particles detached from the vessel due to the supply of the purge gas in addition to the particles detached from the vessel due to the electric discharge started when the exhaust of the gas is permitted, it is possible to surely monitor the particle including, deposits which readily separate, enabling an accurate evaluation of the cleanness in the vacuum apparatus.

In order to achieve the first object, there is provided a particle monitoring method of a vacuum apparatus having a vessel for defining a predetermined space, including the steps of: (a) exhausting a gas from the vessel via a gas exhaust line; (b) monitoring particles within the gas exhaust line; (c) controlling a flow rate of the gas exhausted from the vessel; (d) supplying a purge gas into the vessel via a gas supply line; and (e) controlling a flow rate of the purge gas supplied into the vessel, wherein, in the step (e), a supply of the purge gas is started when an exhaust of the gas is permitted in the step (c), and the monitored particles include the particles detached from the vessel due to the supply of the purge gas.

With the particle monitoring method, since the particles detached from the vessel due to the supply of the purge gas which starts when the exhaust of the gas is permitted are monitored, it is possible to surely monitor the particle including deposits which readily separate, enabling an accurate evaluation of the cleanness in the vacuum apparatus.

The method may further includes the steps of: (f) supplying a corrosive processing gas into the vessel; and exhausting the processing gas from the vessel, wherein, in the step (c), the exhaust of the gas is prohibited when the processing gas is exhausted in the step (g). In this way, by prohibiting the exhaust of the gas via the exhaust line when the processing gas is exhausted via another exhaust line, the corrosion of the particle monitoring unit can be prevented and the life span thereof can be extended.

It is preferable that the flow rate of the purge gas is controlled in the step (e) such that the pressure value of the purge gas becomes at least twice the internal pressure of the vessel. With such method, by controlling the flow rate of the purge gas such that the pressure value of the purge gas becomes at least twice the internal pressure of the vessel, shock wave can be positively generated in the vessel and deposits can be surely detached therefrom.

In order to achieve the first object, there is provided a particle monitoring method of a vacuum apparatus having a vessel for defining a predetermined space, including the steps of: (a) exhausting a gas from the vessel via a gas exhaust line; (b) controlling a flow rate of the gas exhausted from the vessel; (c) monitoring particles within the gas exhaust line; and (d) generating an electric discharge within the vessel, wherein the electric discharge is started when the exhaust of the gas is permitted in the step (b), and the monitored particles include the particles detached from the vessel due to the electric discharge.

With the particle monitoring method, since the particles detached from the vessel due to the electric discharge which starts when the exhaust of the gas is permitted are monitored, it is possible to surely monitor the particle including deposits which readily separate, enabling an accurate evaluation of the cleanness in the vacuum apparatus.

It is preferable that an electromagnetic stress is generated due to the electric discharge in the step (d). In this way, since an electromagnetic stress is generated due to the electric discharge in the vessel, deposits can be positively detached from the vessel.

The method may further includes: (e) supplying a purge gas into the vessel via a gas supply line; and (f) controlling a flow rate of the purge gas supplied into the vessel, wherein, in the step (f), a supply of the purge gas is started when an exhaust of the gas is permitted in the step (b), and the monitored particles include the particles detached from the vessel due to the supply of the purge gas. With the apparatus, since there are monitored the particles detached from the vessel due to the supply of the purge gas in addition to the particles detached from the vessel due to the electric discharge started when the exhaust of the gas is permitted, it is possible to surely monitor the particle including deposits which readily separate, enabling an accurate evaluation of the cleanness in the vacuum apparatus.

In order to achieve the first object, there is provided a program for executing in a computer a particle monitoring method of a vacuum apparatus having a vessel for defining a predetermined space, including: a gas exhaust module for exhausting a gas from the vessel via a gas exhaust line; a particle monitoring module for monitoring particles within the gas exhaust line; a gas exhaust control unit for controlling a flow rate of the gas exhausted from the vessel; a purge module for supplying a purge gas into the vessel via a gas supply line; and a gas supply control unit for controlling a flow rate of the purge gas supplied into the vessel, wherein the gas supply control module starts a supply of the purge gas when the gas exhaust control module permits an exhaust of the gas, and the particles monitored by the particle monitoring module include the particles detached from the vessel due to the supply of the purge gas.

With the program since the particles detached from the vessel due to the supply of the purge gas which starts when the exhaust of the gas is permitted are monitored, it is possible to surely monitor the particle including deposits which readily separate, enabling an accurate evaluation of the cleanness in the vacuum apparatus.

In order to achieve the first object, there is provided a program for executing in a computer a particle monitoring method of a vacuum apparatus having a vessel for defining a predetermined space, including: a gas exhaust module for exhausting a gas from the vessel via a gas exhaust line; a gas exhaust control module for controlling a flow rate of the gas exhausted from the vessel; a particle monitoring module for monitoring particles within the gas exhaust line; and an electric discharge module for generating an electric discharge within the vessel, wherein the electric discharge module starts the electric discharge when the gas exhaust control module permits the exhaust of the gas, and the particles monitored by the particle monitoring module include the particles detached from the vessel due to the electric discharge.

With the program, since the particles detached from the vessel due to the supply of the purge gas which starts when the exhaust of the gas is permitted are monitored, it is possible to surely monitor the particle including deposits which readily separate, enabling an accurate evaluation of the cleanness in the vacuum apparatus.

In order to achieve the second object, there is provided a window member for particle monitoring formed of a transparent member and installed between a housing for defining a predetermined space and a particle monitoring unit for monitoring particles within the housing, wherein the transparent member includes a transparent base; and a surface treatment layer formed by performing a processing on a surface of the base which faces a gas within the housing.

With the window member, since the transparent base member includes a transparent base and the surface treatment layer formed by performing a processing on a surface of the base which faces a gas within the housing, it can efficiently exhibit resistance to active molecules, thereby reducing the frequency of replacement.

It is preferable that the surface treatment layer contains one material selected from a group consisting of carbon, yttrium, yttria and calcium fluoride. Since the surface treatment layer contains one material selected from a group consisting of carbon, yttrium, yttria and calcium fluoride, the window member can efficiently exhibit resistance to the active molecules in the surface treatment layer, thereby positively reducing the frequency of replacement.

It is preferable that the carbon is crystalline diamond or diamond-like carbon.

It is preferable that the content of the selected material ranges from 10 to 100 mass % of the total mass of the surface treatment layer. Since the content of the material constituting the surface treatment layer ranges from 10 to 100 mass % of the total mass of the surface treatment layer. The resistance to the active molecules can be enhanced.

It is preferable that the surface treatment layer contains aluminum or alumina. Since the surface treatment layer contains aluminum or alumina, it can more efficiently exhibit the resistance to the active molecules so that the frequency of replacement can surely reduced.

It is preferable that the content of the aluminum or the alumina ranges from 10 to 100 mass % of the total mass of the surface treatment layer. Since the content of the aluminum or the alumina ranges from 10 to 100 mass % of the total mass of the surface treatment layer, the window member can have an enhanced resistance to the active molecules.

It is preferable that the processing is a coating processing. Since the preset processing is a coating processing, it is possible to form the surface treatment layer on the base with ease.

It is preferable that the processing is a doping processing. Since the preset processing is a doping processing, it is possible to positively form the surface treatment layer on the base.

It is preferable that the thickness of the surface treatment layer ranges from 100 nm to 10 μm. Since the thickness of the surface treatment layer ranges from 100 nm to 10 μm, the resistance to the active molecules can be enhanced.

It is preferable that the base is formed of glass containing silicon as a primary component, and the surface treatment layer is exposed to active molecules included in a gas within the housing. In this way, since the base is formed of glass containing silicon as a primary component, and the surface treatment layer is exposed to active molecules included in a gas within the housing, the surface treatment layer can more efficiently exhibit the resistance to the active molecules while preventing the silicon from being exposed to the plasma atmosphere, thereby positively reducing the frequency of replacement.

In order to achieve the second object, there is provided a window member for particle monitoring formed of a transparent member and installed between a housing for defining a predetermined space and a particle monitoring unit for monitoring particles within the housing, wherein the transparent member is formed of calcium fluoride.

With the window member, since the transparent member is formed of calcium fluoride, it can efficiently exhibit resistance to active molecules, thereby reducing the frequency of replacement.

It is preferable that the housing is formed of a vessel or a tube.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, preferred embodiments of the present invention will be described in detail with reference to accompanying drawings.

Figure 1:
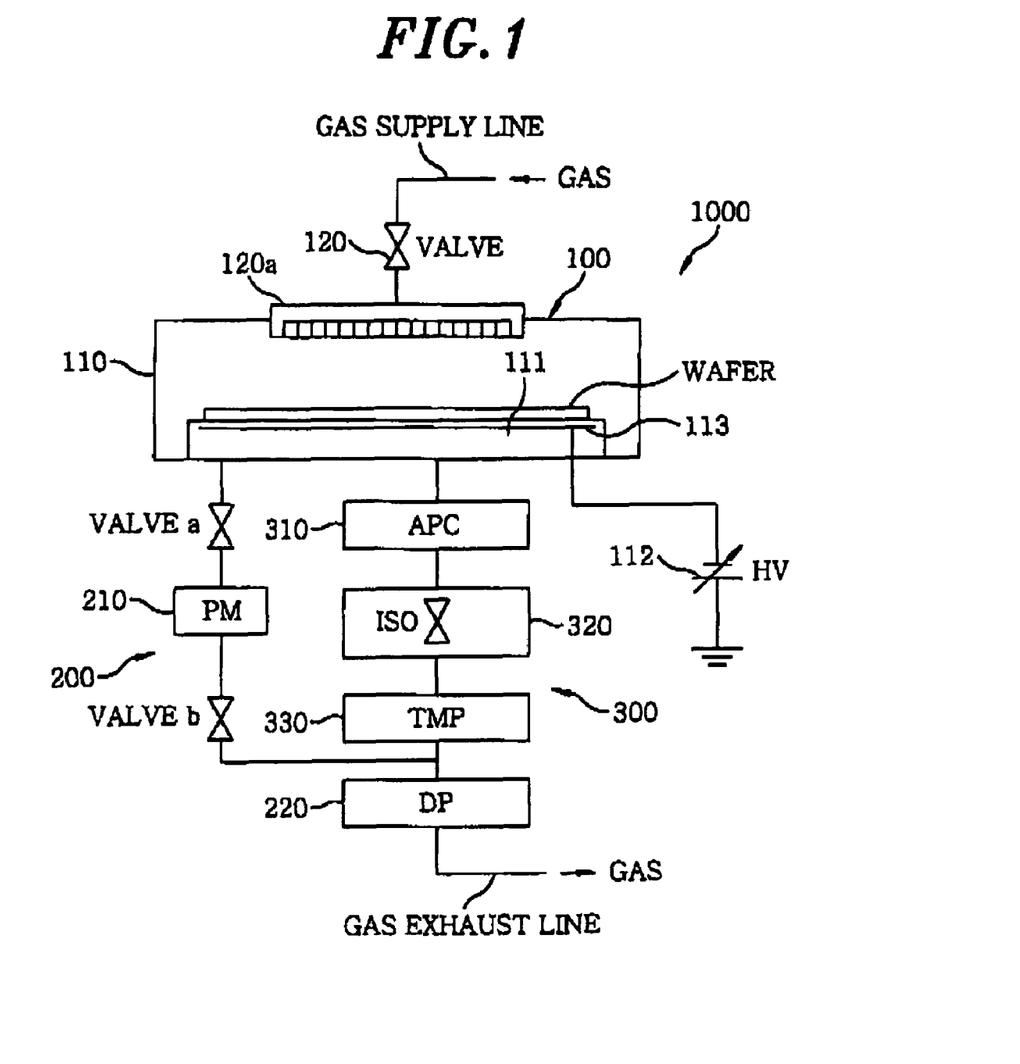
FIG. 1 is a schematic configuration view of a semiconductor manufacturing apparatus including a vacuum apparatus in accordance with a first preferred embodiment of the present invention.

FIG. 1 is a schematic configuration view of a semiconductor manufacturing apparatus 1000 including a vacuum apparatus in accordance with a first preferred embodiment of the present invention.

As shown in FIG. 1, the semiconductor manufacturing apparatus 1000 has a processing chamber (vacuum apparatus) 100 formed of a cylindrical vessel for performing a manufacturing processing, such as etching, sputtering, chemical vapor deposition (CVD) or the like, on a semiconductor wafer (hereinafter, referred to as "wafer"), which serves as a substrate to be processed, by using plasma. The processing chamber 100 is connected to a load lock chamber having a wafer transfer arm by which the wafer is loaded into the processing chamber 100.

The processing chamber 100 includes a chamber wall 110 for defining a space necessary for performing a manufacturing processing and a wafer stage 111 installed on a bottom surface of the processing chamber 100. An electrode 113 connected to a high voltage power supply 112 is buried in the wafer stage 111, and if a high voltage HV from the high voltage power supply 112 is applied to the electrode 113, the electrode 113 electrostatically attracts and holds (chucks) the wafer loaded on the wafer stage 111 by the transfer arm. A shower head 120a with a number of through holes is installed at an upper portion of the processing chamber 100 to introduce a corrosive processing gas into the processing chamber via the through holes.

Further, a gas supply line formed of a tubular member is connected to the upper portion of the processing chamber 100 to introduce a purge gas into the processing chamber 100. On the gas supply line, there is installed a valve 120 for controlling the flow rate of the purge gas to be supplied into the processing chamber 100.

A gas of low corrosiveness, high obtainability and low price is used as the purge gas. For example, a nitrogen gas ($N_2$), a helium gas (He), an argon gas (Ar), a dry air, oxygen (O$_2$) or the like can be employed as the purge gas. Here, a halogen gas is not proper as a purge gas since it corrodes glass components of a particle monitoring unit to be described later.

Connected to lower portions of the processing chamber 100 are a rough pumping line 200 formed of a thin tubular member with a diameter of, for example, 25 mm and a main vacuum pumping line 300 formed of a thick tubular member with a diameter of, for example, 150 mm. The rough pumping line 200 and the vacuum pumping line 300 are merged into a gas exhaust line. The gas exhaust line exhausts gases from the rough pumping line 200 and/or the main vacuum pumping line 300 out of the semiconductor processing apparatus 1000.

Installed on the rough pumping line 200 are a dry pump (DP) 220 for pumping out a gas from the processing chamber 100 via the gas exhaust line; valves a and b for controlling the flow rate of the gas exhausted by the dry pump 220, i.e., the flow rate of the gas introduced into the gas exhaust line from the processing chamber 100; and an optical particle monitoring unit (PM) 210 for monitoring particles between the valves a and b.

On the main vacuum pumping line 300, an automatic pressure controller (APC) 310 for monitoring the internal pressure of the processing chamber 100, an isolation valve (ISO) 320 serving as a gate valve, and a turbo molecular pump (TMP) 330 connected to the dry pump 220 are installed in that order from the side of the processing chamber 100. The isolation valve 320 regulates the evacuation of the processing chamber 100 by the turbo molecular pump 330. The automatic pressure controller 310 controls the degree of regulation by the isolation valve 320, while monitoring the internal pressure of the processing chamber 100. The turbo molecular pump 330 has a gas pumping rate greater than that of the dry pump 220.

In the semiconductor manufacturing apparatus 1000, when depressurizing the processing chamber 100 for a manufacturing processing, the processing chamber 100 is first evacuated via the rough pumping line 200 until the internal pressure of the processing chamber 100 reaches a preset pressure level and then, after closing the valves a and b, the processing chamber 100 is evacuated to a desired pressure or vacuum level through the main vacuum pumping line 830, while monitoring the internal pressure of the processing chamber 100 by mean of the automatic pressure controller 310. The vacuum pumping via the main vacuum pumping line 300 is continued during the manufacturing processing because the corrosive processing gas is supplied into the processing chamber 100 via the shower head 120$a$.

Figure 2:
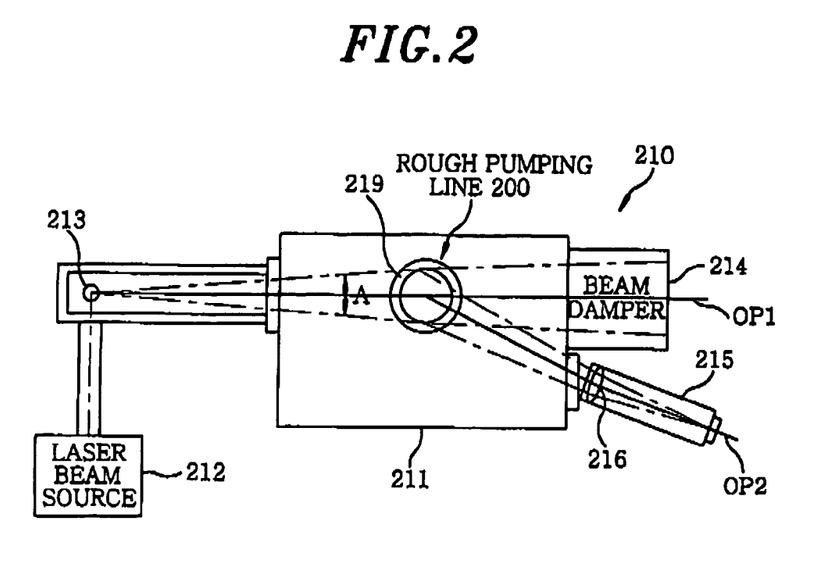
FIG. 2 sets forth a schematic configuration view of a particle monitoring unit of FIG. 1.

FIG. 2 provides a schematic configuration view of the particle monitoring unit 210 shown in FIG. 1.

As shown in FIG. 2, the particle monitoring unit 210 includes a housing 211 disposed to surround the periphery of the rough pumping line 200; a laser beam source 212 for emitting a laser beam of a wavelength in the range of, for example, a visible ray; a mirror 213 for directing the laser beam emitted from the laser beam source 212 to the rough pumping line 200 inside the housing 211; a beam damper 214 at which the beam arrives after passing through the rough pumping line 200; a light receiving member 215 for receiving laser beams scattered by particles, which flow through the rough pumping line 200, via a window member 219 for particle monitoring disposed at a certain part of the rough pumping line 200; and a lens 216 for focusing the scattered laser beams which are incident upon the light receiving member 215. The window member 219 is formed of quartz. The particle monitoring unit 210 detects the laser beam received by the light receiving member 215 as a detection signal, as will be described later with reference to FIG. 3. As shown in FIG. 2, the light receiving member 215 is disposed at a predetermined angle with respect to the incident direction (optical axis OP1 to be described later) of the laser beam. That is, an optical axis of scattered beams OP2 lies at a preset angle with respect to the optical axis OP1. Further, the window member 219 for particle monitoring forms a part of the rough pumping line 200.

At least a part of the rough pumping line 200 onto which a laser beam is irradiated is made of quartz glass whose surface is partially or entirely coated with an antireflection film formed of magnesium fluoride (MgF$_2$), wherein the quartz glass serves as the window member 219 for particle monitoring.

The mirror 213 is configured to perform a raster scanning of the entire region of the inner diameter of the rough pumping line 200's cross section within a range A around the optical axis OP1 by using the laser beam irradiated from the laser beam source 212. Moreover, as the beam damper 214, a black solid body having a surface with irregularities, an object with an optical labyrinth structure and the like may be used. Further, a photomultiplier tube (PMT), a charge coupled device (CCD) or the like can be used as the light receiving member 215.

Figure 3:
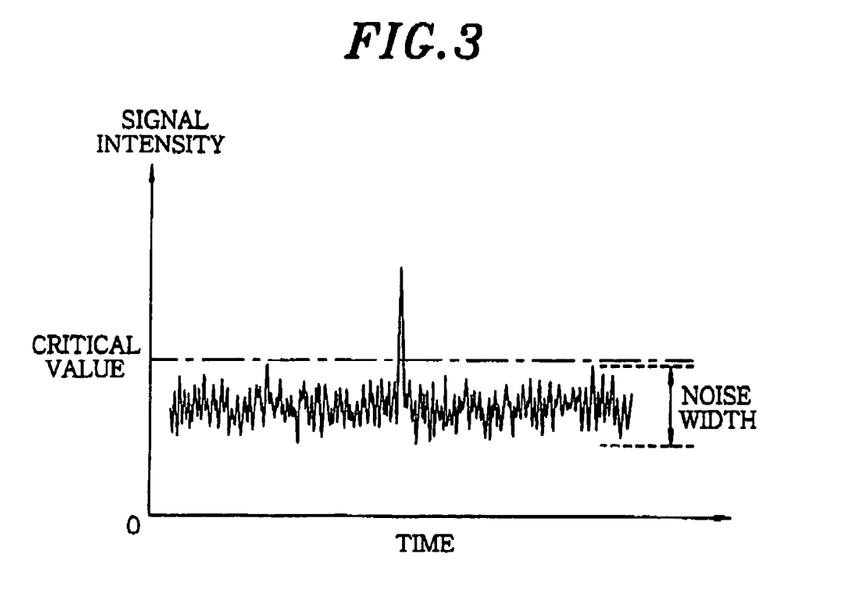
FIG. 3 provides a graph to describe the intensity of a signal detected by a light receiving member of the particle monitoring unit of FIG. 2.

FIG. 3 is a graph describing the intensity of a detection signal detected by the light receiving member 215 of the particle monitoring unit 210 in FIG. 2.

As shown in FIG. 3, the signal detected by the light receiving member 215 normally includes a noise signal generated due to a stray light. Since the noise signal has a predetermined noise width, a threshold value of signal intensity is set in the particle monitoring unit 210 by adding a preset margin value to an upper limit of the noise width.

The particle monitoring unit 210 counts detection signals having intensities greater than the threshold value as particles, and based on the counted number of particles, the cleanness of the processing chamber 100 can be evaluated.

Figure 4:
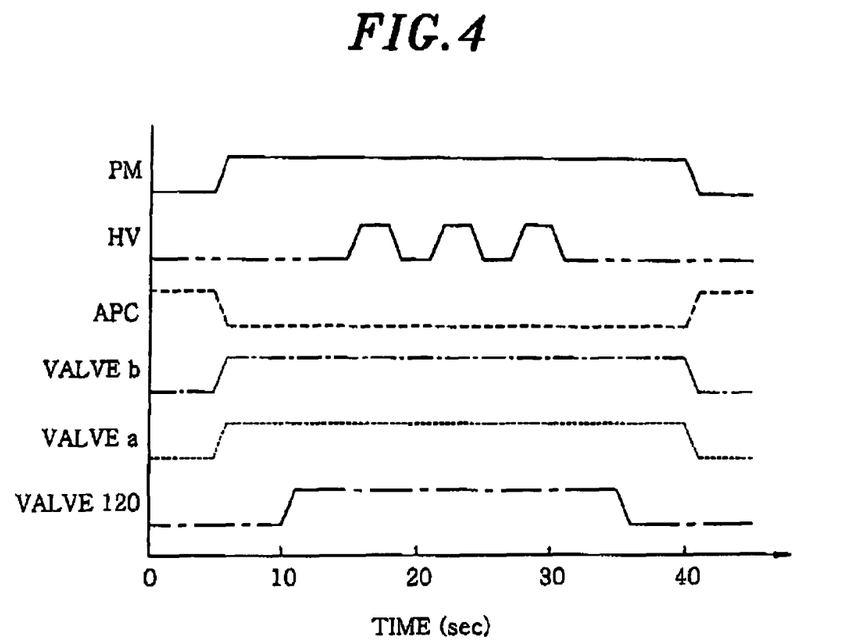
FIG. 4 presents a timing chart for explaining the sequence of a particle monitoring method performed by the semiconductor manufacturing apparatus of FIG. 1.

FIG. 4 provides a timing chart to describe a sequence of a particle monitoring method performed by the semiconductor manufacturing apparatus 1000 in FIG. 1.

As shown in FIG. 4, when performing a particle monitoring after the manufacturing processing has been completed and the wafer has been unloaded from the processing chamber 100, the particle monitoring unit 210 is powered on and the valves a and b on the side of the processing chamber 100 are opened. At the same time, the automatic pressure controller 310 is turned off and the isolation valve 320 (not shown) is closed. As a result, the evacuation of the processing chamber 100 via the main vacuum pumping line 300 is converted into an evacuation via the rough pumping line 200.

Thereafter, the valve 120 is opened, and a purge gas is supplied into the processing chamber 100 via the gas supply line at a flow rate of, for example, 70 L/min (70000 SCCM), which is higher than that of a purge gas for a conventional purge gas cleaning. Typically, since the manufacturing processing is carried out in the processing chamber 100 under the high vacuum atmosphere of, for example, $10^{-1} \sim 10^{-4}$ Pa, the purge gas is rapidly introduced into the processing chamber at a pressure level higher than the internal pressure of the processing chamber 100, resulting in an increase in the internal pressure of the processing chamber 100. A pressure in the processing chamber 100 which finally reaches a stable value by such pressure increment is preferably 133.3 Pa (1 Torr) or greater. By setting the stable pressure value to be 133.3 Pa or greater, the exhaust gas from the processing chamber 100 is given a high viscous force, thus facilitating the discharge of particles therewith.

Thus, the rapid inflow of the purge gas causes physical vibration of all objects in the processing chamber 100, that is, the chamber wall 110 and the wafer stage 111, due to a shock wave.

Further, the pressure value of the purge gas supplied into the gas supply line is preferably set to be more than twice the internal pressure of the processing chamber 100, to apply the vibration to the objects in the processing chamber 100 securely.

Afterward, under the condition that the valve 120 is opened, a high voltage HV is applied to the electrode 113 from the high voltage power supply 112 three times. The application of the high voltages will be described later in accordance with a second preferred embodiment of the present invention.

When the particle monitoring is completed, the valves 120, a and b are closed in sequence and the isolation valve 320 is opened, to thereby return to the state immediately after the completion of the manufacturing processing.

Since the above-described sequence of the particle monitoring method is performed after the manufacturing processing has been completed and the wafer has been unloaded from the processing chamber 100, contamination of the wafer can be prevented. Moreover, it is preferred that the particle monitoring is conducted at a time when the processing gas is not used, to prevent the corrosion of the glass components of the particle monitoring unit 210.

Referring to FIG. 4, when performing the particle monitoring, physical vibration (shock wave) due to the purge gas is applied to the objects within the processing chamber 100.

Figure 5:
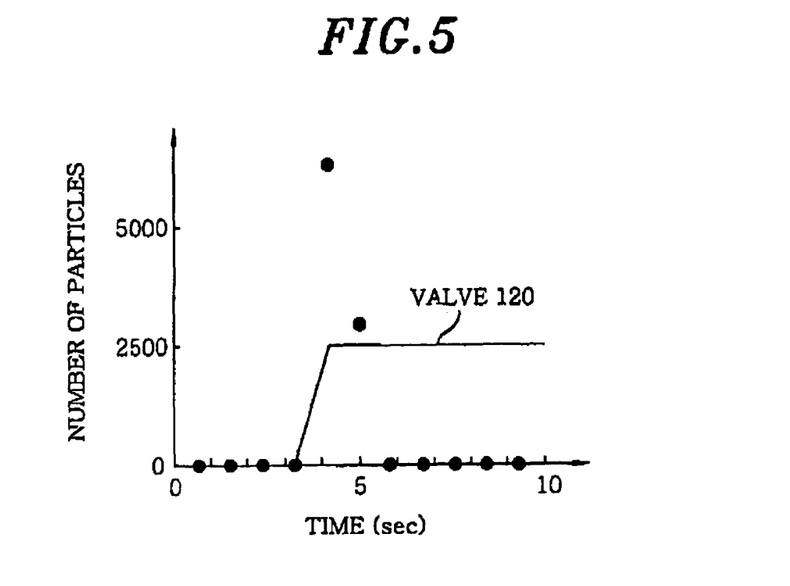
FIG. 5 depicts a graph to identify the number of particles measured by the particle monitoring unit, for example, when performing the sequence of FIG. 4.

FIG. 5 is a graph showing the number of particles measured by the particle monitoring unit 210, for example, through the sequence in FIG. 4. Note, however, that the time axes of FIGS. 4 and 5 are not intended to align in these graphs, but rather FIG. 5 merely shows an example of measurements shortly before and after the introduction of purge gas. More specifically, FIG. 5 illustrates an example of measurement results obtained before and after the occurrence of vibrations due to the purge gas.

As shown in FIG. 5, a number of, for example, 9000, particles are counted for several seconds after the valve 120 is opened. This is because deposits detached from the chamber wall 110, the wafer stage 111, and so forth were also counted as particles. Thus, by monitoring the particles including the deposits, the cleanness of the processing chamber 100 can be evaluated precisely. Moreover, the duration of opening the valve 120 is set to be 1 to 5 seconds and preferably 2 to 5 seconds, to obtain a time period long enough to allow the vibration to diffuse through the processing chamber 100 sufficiently.

Referring to FIGS. 4 and 5, by applying the physical vibration due to the purge gas to the objects in the processing chamber 100 at least one time by way of opening the valve 120, detachment of deposits is facilitated, thus enabling accurate monitoring of particles and evaluation of the cleanness of the processing chamber 100.

Moreover, the particle monitoring is conducted after completing the manufacturing processing of the wafer. Thus, by maintaining the valve a closed during the manufacturing processing, the inflow of the processing gas into the particle monitoring unit 210 can be prevented, so that corrosion of the glass components of the particle monitoring unit 210 can be prevented. Consequently, the life span of the particle monitoring unit 210 can be lengthened and the productivity of the semiconductor manufacturing apparatus 1000 can be improved.

Though the first embodiment uses physical vibration generated by the supply of the purge gas, any type of vibration other than may also be used. For example, it is also preferable to apply ultrasonic waves of tens of kHz into the processing chamber 100 in order to generate vibration. Further, in case of utilizing the physical vibration, the gas supply line is preferred to have no orifice structure at a joint where it is connected with the processing chamber 100 or a vacuum transfer chamber 100' to be describe later.

Moreover, it is preferable to generate physical vibration plural times. In such a case, since detachment of deposits reduces every time when the generation of physical vibration is repeated, the number of particles detected tends to be reduced. Thus, it is possible to perform a next manufacturing processing after the cleanness of the processing chamber 100 is evaluated as high.

The above first embodiment is preferably performed combined with the second embodiment to be described later, as shown in FIG. 4.

Since the configuration of a semiconductor manufacturing apparatus having a vacuum apparatus in accordance with the second embodiment is identical to that of the first embodiment, explanation thereof will be omitted; and only a distinctive feature of a particle monitoring method of a semiconductor manufacturing apparatus 1000 will be described.

A semiconductor manufacturing apparatus 1000 in accordance with the second embodiment intermittently applies a high voltage HV to an electrode 113, for example, three times from a high voltage power supply 112. The applied high voltages HV are preferably not smaller than +1 kV or not greater than −1 kV. More preferably, a voltage of +1 kV and a voltage of −1 kV are applied alternately. As a result of applying the high voltages in this manner, an electromagnetic stress to be described below can be generated efficiently.

Whenever the high voltage HV is applied, a direct current (DC) discharge occurs instantaneously within the processing chamber 100, whereby a momentary potential gradient is formed on the chamber wall 110 or the wafer stage 111, thus creating an electromagnetic stress. Due to thus created electromagnetic stress, deposits on the chamber wall 110 or the wafer stage 111 are detached therefrom, and the detached deposits are discharged as particles along with the purge gas, to be detected by the particle monitoring unit 210.

When the high voltage HV is applied one time, the number of particles counted by the particle monitoring unit 210 varies with time in a manner similar to that shown in FIG. 5. The number of counted particles tends to be reduced every time the number of intermittent application of the high voltage HV increases, for detachment of deposits reduces with the repetition of the HV application. Accordingly, it is preferable to perform the application of the high voltage HV one to ten times and, more preferably, two to five times.

In accordance with the second embodiment, detachment of deposits is facilitated by applying a high voltage HV at least one time, so that more accurate particle monitoring is possible, thus enabling exact evaluation of the cleanness of the processing chamber 100.

Moreover, by repeating the intermittent application of the high voltage HV is repeated plural times, it is possible to perform a next manufacturing processing after the cleanness of the processing chamber 100 is evaluated as high.

Furthermore, though the application of the high voltage HV is carried out while the valve 120 is opened, as shown in FIG. 4, it is also possible to maintain the valve 120 closed during the HV application. In such a case, vibration of, for example, a wafer due to a purge gas from a gas supply line can be prevented.

In addition, though a high voltage HV is applied to form the momentary potential gradient on the chamber wall 110 or the wafer stage 111, application of a high frequency RF (radio frequency) is also preferable. By the application of the RF, an RF discharge occurs, thereby resulting in an electromagnetic stress, as in the case of applying the high voltage HV. In case of using the RF, the duration of the RF discharge is preferably set to be not too long: for example, it is preferably set to be about one second.

The second embodiment is preferably performed combined with the first embodiment, as illustrated in FIG. 4.

In the above-described first and the second embodiment, though the gas exhaust line connected to the processing chamber 100 is configured as a dual pumping system including the rough pumping line 200 and the main vacuum pumping line 300, a triple or more pumping system is also preferable. Further, a case of a single exhaust line will be described hereinbelow as a third preferred embodiment of the present invention.

Figure 6:
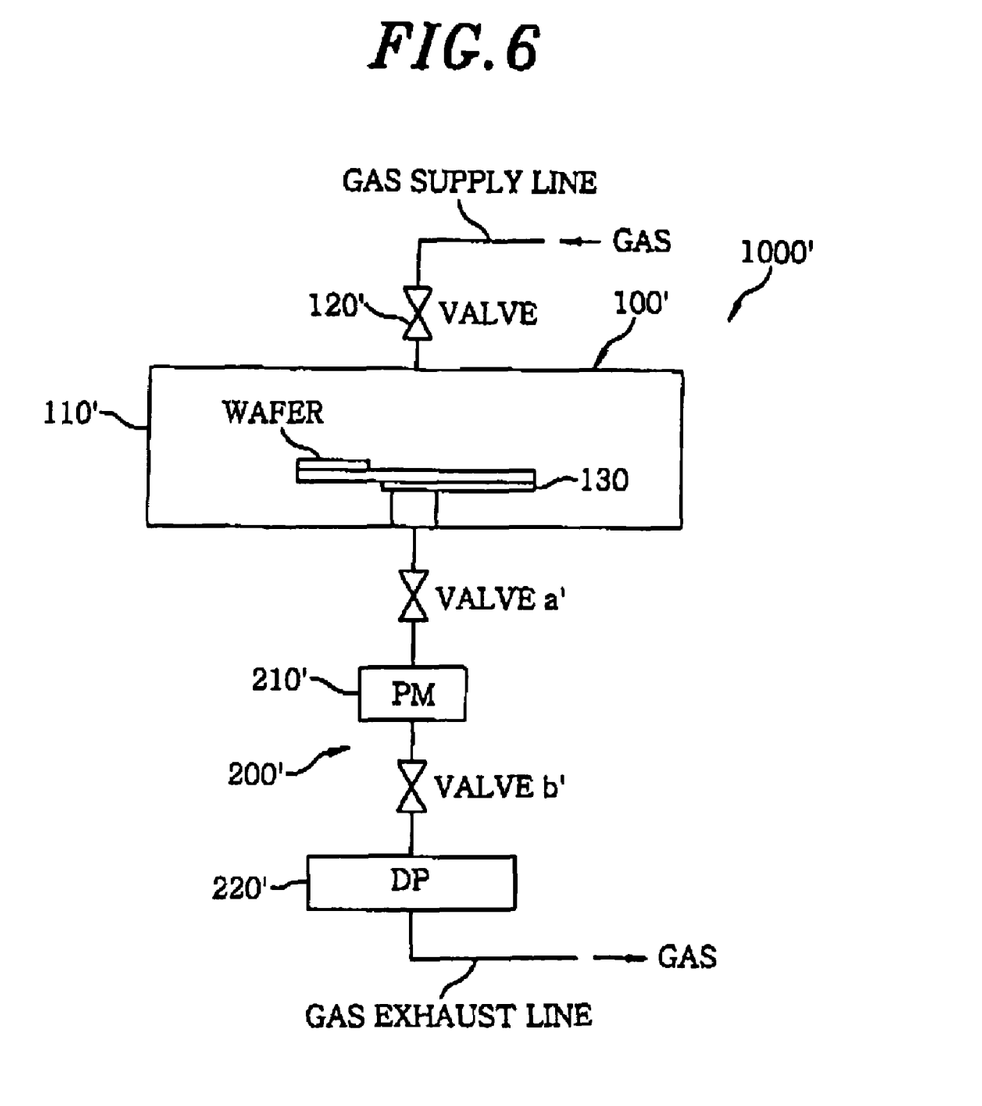
FIG. 6 offers a schematic configuration view of a semiconductor manufacturing apparatus including a vacuum apparatus in accordance with a third preferred embodiment of the present invention.

FIG. 6 illustrates a schematic configuration of a semiconductor manufacturing apparatus having a vacuum apparatus in accordance with the third preferred embodiment of the present invention.

In FIG. 6, a vacuum transfer apparatus 1000' serving as a vacuum apparatus includes a vacuum transfer chamber 100' provided with a single exhaust line. The vacuum transfer chamber 100' is employed to, for example, a load lock chamber connected to the processing chamber 100 of the semiconductor manufacturing apparatus 1000 in FIG. 10, and the load lock chamber has a transfer arm for transferring wafers. The vacuum transfer apparatus 1000' transfers a wafer onto the wafer stage 111 in the processing chamber 100 by using an arm 130.

Connected to the vacuum transfer chamber 100' is a gas supply line with a valve 120' and a gas exhaust line 200' with a dry pump 220', valves a' and b', and a particle monitoring unit 210' installed between the valves a' and b'.

The configuration of the third embodiment closely resembles that of the first embodiment except that the main vacuum pumping line 300 is omitted. Thus, likes parts will be assigned like reference numerals, and description thereof will be omitted, while elaborating only distinctive parts.

Figure 7:
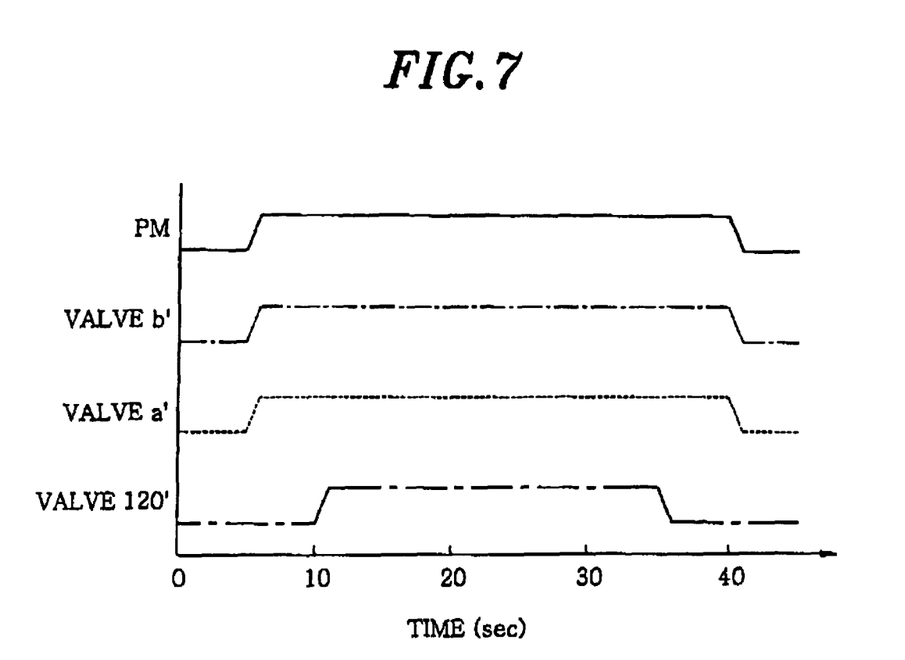
FIG. 7 sets forth a timing chart for explaining the sequence of a particle monitoring method performed by a vacuum transfer apparatus of FIG. 6.

Since the turbo molecular pump 330 on the main vacuum pumping line 300 is not installed in the vacuum transfer chamber 100', the vacuum transfer chamber 100' is not in a high vacuum state when a particle monitoring is performed. In such a case, a sequence as described in FIG. 7 is performed after a certain vacuum level is obtained by means of the dry pump 220'. Since the sequence in FIG. 7 is identical to that explained in FIG. 4, description thereof will be omitted.

Referring to FIGS. 6 and 7, by applying physical vibration of due to a purge gas to objects in the vacuum transfer chamber 100' after opening the valve 120', detachment of deposits can be facilitated, thus enabling accurate particle monitoring and evaluation of the cleanness of the vacuum transfer chamber 100'.

Moreover, though the vacuum transfer chamber 1000' has been described to have the single exhaust line in the third embodiment, but it may have multiple exhaust lines. In case of multiple exhaust lines, though the multiple exhaust lines have normally different conductances (the conductance represents a coefficient indicating the fluidity of a fluid such as a discharged gas), any exhaust line of any conductance may employ this embodiment.

Further, it is preferable to combine the third embodiment with the second embodiment. In this case, a high voltage power supply identical to the high voltage power supply 112 is connected to the objects in the vacuum transfer chamber 100'.

In accordance with the first to the third embodiment descried above, though the cleanness of the processing chamber 100 or the vacuum transfer chamber 100' is inspected under the absence of a wafer therein, it is also possible to evaluate the cleanness of an object other than the processing chamber 100 or the vacuum transfer chamber 100', for example, the cleanness of a wafer therein.

For example, the cleanness of the processing chamber 100 is first evaluated. Then, if the cleanness is found to be sufficiently high and there is detected no more detachment of particles, a wafer is loaded into the processing chamber 100 and the cleanness of the processing chamber 100 is evaluated again upon the presence of the wafer. Thereafter, by comparing the two evaluation results, the cleanness of the wafer can be determined. Likewise, by comparing evaluation results of two cases where a rear surface of the wafer is in contact with the wafer stage 111 and is not, the cleanness of the rear surface of the wafer can be examined.

Though a particle monitoring is performed after completing a manufacturing processing in the first to the third embodiment, it is also possible to monitor particles prior to or during the manufacturing processing.

Moreover, though the gas supply line has been described to have no orifice structure at a joint where it is connected to the processing chamber 100 or the vacuum transfer chamber 100', the gas supply line with an orifice structure may be employed in a case where a wafer or the like exists in the processing chamber 100 or the vacuum transfer chamber 100'. Accordingly, a damage of, e.g., the wafer due to physical vibration imposed thereon by the purge gas can be prevented.

Further, though the window member 219 for particle monitoring shown in FIG. 2 is formed of quartz in the above-described preferred embodiments, it may be formed of any material as long as it is transparent.

Moreover, the object of the present invention can also be accomplished by providing a computer, for example, a PC 600 shown in FIG. 9 to be described later with a storage medium having therein program codes (corresponding to the sequence in FIG. 4 or 7) of software for realizing the functions of the preferred embodiments described above. In this case, the computer (or CPU, MPU, or the like) reads the program codes stored in the storage medium and executes them.

In addition, besides the mechanism of directly realizing the functions of the above embodiments by executing the program codes read by the computer, for example, the PC 600, it is also possible to set an operating system (OS) working on the PC 600 to perform an actual processing partially or entirely based on instructions of the program codes and realize the functions of the embodiments through such processing.

Furthermore, the program codes read from the storage medium can be recorded in a memory provided in a function extension card inserted into the PC 600 or in a function extension unit connected to the computer. Then, based on the instructions of the program code, a CPU or the like included in the function extension card or the function extension unit performs an actual processing partially or entirely, and the functions of the above preferred embodiments can be carried out by such processing.

Further, as long as the program realizes the functions of the above preferred embodiments through the PC 600, it may be of an object code type or a script data type supplied into the OS, or it may be a program executed by an interpreter.

The storage medium for storing the program therein may be, for example, a RAM, a NV-RAM, a floppy (registered trademark) disk, an optical disk, a magneto-optical disc, a CD-ROM, a CD-R, a CD-RW, a DVD (DVD-ROM, DVD-RAM, DVD-RW, DVD+RW), a magnetic tape, a nonvolatile memory card, a ROM, and the like. Alternatively, the program may be downloaded from a computer or a database (not shown) connected to the Internet, a commercial network, a local area network, or the like.

Hereinafter, a window member for particle monitoring in accordance with a fourth preferred embodiments of the present invention will be described.

Figure 8:
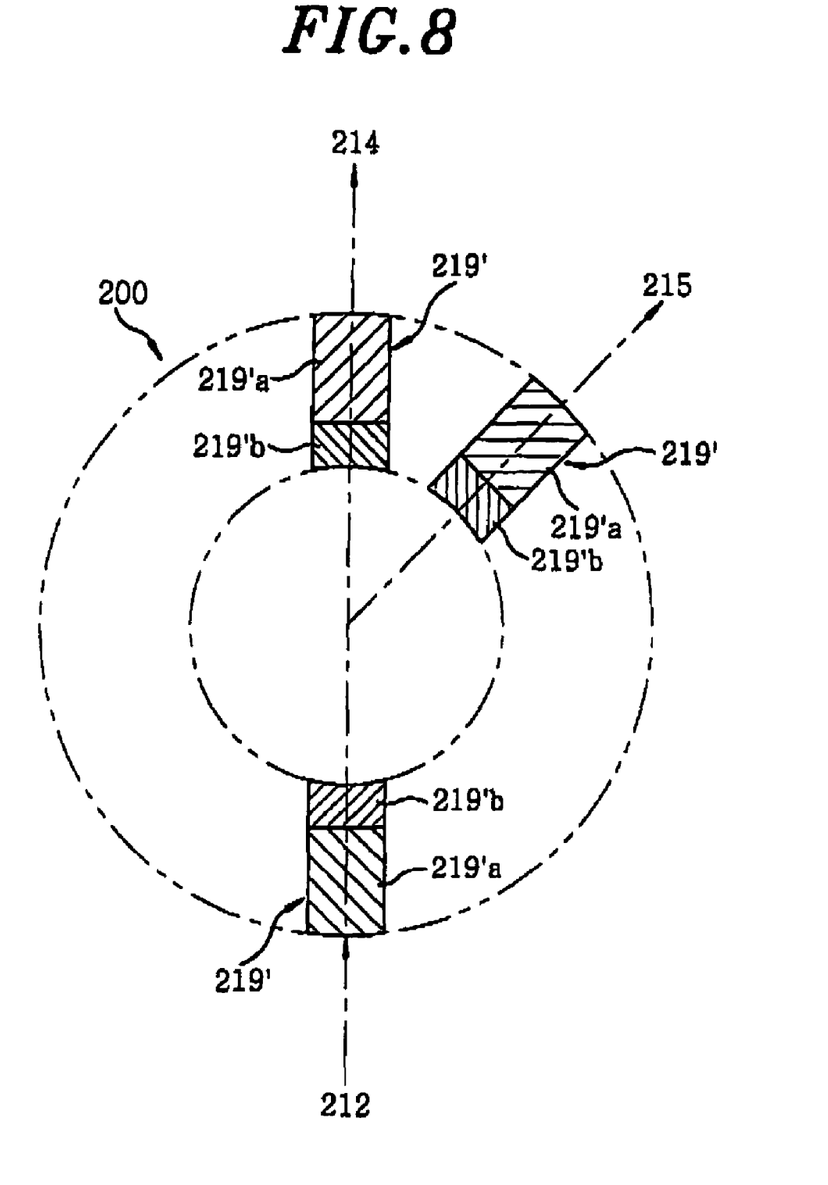
FIG. 8 presents a detailed configuration view of a window member for particle monitoring in accordance with a fourth preferred embodiment of the present invention.

FIG. 8 provides a detailed cross sectional view to illustrate the configuration of the window member for particle monitoring.

The window member in accordance with the fourth embodiment is employed in lieu of the window member 219 for particle monitoring formed of quartz in accordance with the first embodiment. Further, in the below description, parts identical to those of the semiconductor manufacturing apparatus 1000 in accordance with the first embodiment will be assigned like reference numerals, and explanation thereof will be omitted.

In FIG. 8, each of window members 219' for particle monitoring has a substantially columnar shape and is disposed between a rough pumping line 200 and a particle monitoring unit 210. Specifically, the window members 219' are inserted into complementary openings provided in the rough pumping line 200. Here, the window members 219' are not limited to the substantially columnar shapes to be inserted into the respective openings of the rough pumping line 200, but may have, for example, a hollow cylindrical shape of a diameter approximately identical to that of the rough pumping line 200, while forming a part of the rough pumping line 200.

Moreover, each window member 219' has a transparent base 219'a and a surface treatment layer 219'b obtained by performing a surface treatment on the base 219'a. The base 219'a has a gas contact surface contacting a gas within the rough pumping line 200 and a monitor surface connected to the particle monitoring unit 210. The surface treatment layer 219'b is formed by performing a surface treatment to be described below on the gas contact surface of the base 219'a.

Though the base 219'a is preferably formed of glass containing silicon as its principal component, for example, quartz, it may be also formed of a transparent resin.

The surface treatment layer 219'b contains a material selected from a group consisting of carbon (C), yttrium (Y), yttria ($Y_2O_3$), calcium fluoride ($CaF_2$), aluminum (Al) and alumina ($Al_2O_3$). In case the material is carbon, crystalline diamond or diamond-like carbon is preferable. By using these materials, resistance to halogen-based plasma (hereinafter, referred to as "plasma resistance") or resistance to active molecules can be improved sufficiently.

Among the above group of materials, calcium fluoride has physical characteristics as follows: insolubility in water, a melting point of 1373° C., maximum usable temperature of 900° C., a hardness of a value of 158.3 expressed by Knoop number, transmissive light wavelength range of 0.2 to 9.0 μm and a refractive index of 1.39 against the light with a wavelength of 1000 $cm^{-1}$. Besides, calcium fluoride has high corrosion-resistance against halogen, and also has a high pressure-resistance due to its great hardness. Furthermore, it is easy to attain calcium fluoride with high purity at a low price. Also, calcium fluoride is hard to dissolve in an aqueous solution of hydrogen fluoride, i.e., hydrofluoric acid than quartz is.

Among the above-specified materials, calcium fluoride is adequate to form the window members surface treatment layer 219' b since it has high pressure-resistance. Moreover, since its maximum usable temperature is 900° C., it is adequate for use in the processing chamber 100 which is in a high-temperature atmosphere of about 900° C. Besides, due to its transmissive light wavelength range larger than that of quartz, it is adequate for optical measurement. Accordingly, it is most preferable to use calcium fluoride.

Further, individual aluminums and aluminum atoms among alumina react with fluorine among plasma, thus generating aluminum fluoride ($AlF_3$). Since so generated aluminum fluoride remains on the surface treatment layer 219'b, plasma resistance against fluorine becomes particularly high.

Moreover, the halogen-based plasma contains halogen that corrodes quartz glass or a compound thereof. For example, the halogen-based plasma may be a fluorine-based plasma including fluorine or a compound thereof, such as $CF_4$/Ar/$O_2$/CO plasma, $F_2$ plasma, carbon fluoride-based plasma such as $CF_4$, $C_4F_8$ and $C_5F_8$, and chlorine ($Cl_2$) plasma. These halogen-based plasma contains active molecules such as halogen radicals that react with silicon atoms of glass or the like, resulting in deterioration of the glass or the like.

Furthermore, the content of the material forming the surface treatment layer 219'b is preferably set to range from 10 to 100 mass % of the total mass of the surface treatment layer 219'b. In case the content of the material is less than 10 mass %, the resistance of the surface treatment layer 219'b to the plasma or the active molecules cannot be improved sufficiently.

Further, the thickness of the surface treatment layer 219'b preferably ranges from 100 nm to 100 μm. If the thickness is smaller than 100 nm, the surface treatment layer 219'b tends to be readily separated from the base 219'a in case the surface treatment layer 219'b is formed of a coating film to be described later or tends to be readily corroded by the fluorine-based plasma in case it is formed of a doping layer. Meanwhile, if the thickness of the surface treatment layer 219'b is larger than 100 μm, its formation on the base 219'a becomes difficult so that the manufacturing cost thereof is increased, and further the transparency of the surface treatment layer 219'b reduces, thus making it difficult to monitor particles within the gas exhaust line by means of the particle monitoring unit 210.

Hereinafter, the surface treatment of the gas contact surface of the base 219'a will be described.

The surface treatment includes a coating processing for forming a coating film made of the same material as that of the surface treatment layer 219'b on the gas contact surface of the base 219'a and a doping processing for forming a doping layer by way of doping the same material as that of the surface treatment layer 219'b up to a preset depth from the gas contact surface. Meanwhile, besides the coating and the doping processing, other methods may also be employed.

The coating processing includes, e.g., a method for melting a mixture of the above materials such as silicon dioxide, aluminum oxide and the like and cooling it rapidly on the gas contact surface of the base 219'a, a spraying method for spraying the mixture in fusion onto the gas contact surface of the base 219'a and a method for forming a film made of the above materials by a sputtering or a PVD. By performing the coating processing, it is possible to form the surface treatment layer 219'b on the base 219'a easily.

The doping processing includes, e.g., an ion implantation method or a method for partially melting the gas contact surface of the base 219'a to mix it with the above materials. Further, it is preferred to perform a baking after doping the above materials. Also, though the interface between the surface treatment layer 219'b and the base layer 219'a is not definitely distinguishable in case the surface treatment layer 219'b is formed on the base 219'a by doping, the content of the doped materials preferably needs to be in the above-specified content range at least at a preset depth from the gas contact surface of the surface treatment layer 219'b. Since the surface treatment layer 219'b is hardly detached from the base 219'a when it is formed by doping, the surface treatment layer 219'b is positively formed on the base 219'a.

With the window member 219' for particle monitoring in FIG. 8, since the surface treatment layer 219'b is formed on the base 219'a, the surface treatment layer 219'b serving as a new gas contact surface efficiently exhibits resistance to plasma or active molecules. Accordingly, the frequency of replacing the window member 219' can be reduced. Moreover, with the decrease of the frequency of replacement, it is possible to make the time period for maintaining the vacuum pressure in the gas exhaust line 200 longer, whereby the productivity of the semiconductor manufacturing apparatus 1000 can be improved.

In addition, since the window members 219' for particle monitoring have resistance to plasma or active molecules such that their deterioration is suppressed, the particle monitoring unit 210 can surely monitor particles including detached deposits, enabling exact evaluation of the cleanness of the semiconductor manufacturing apparatus 1000.

Moreover, in the fourth embodiment of the present invention, the window member 219' for particle monitoring in FIG. 8 preferably has high transparency with respect to the laser beam of a wavelength in the range of visible ray, which is emitted from the laser beam source 212. Also, the window member 219' preferably has enough hardness to be used to face the vacuum space.

Further, a film of magnesium fluoride may also be formed on the monitor surface of the base 219'a, to thereby prevent reflections of light incident on the window members 219' for particle monitoring.

Further, though the window member 219' for particle monitoring in FIG. 8 has been described to include the base 219'a and the surface treatment layer 219'b in the fourth preferred embodiment, it may be formed of a single bulk member made of calcium fluoride.

Also, the above-descried window members 219' for particle monitoring can be used in another vacuum vessel, for example, the processing chamber 100 in FIG. 1 or a housing such as the particle monitoring unit 210 or a piping in FIG. 6. Besides, it may be used in another unit other than the particle monitoring unit. A specific example thereof will be described with reference to FIG. 9.

Figure 9:
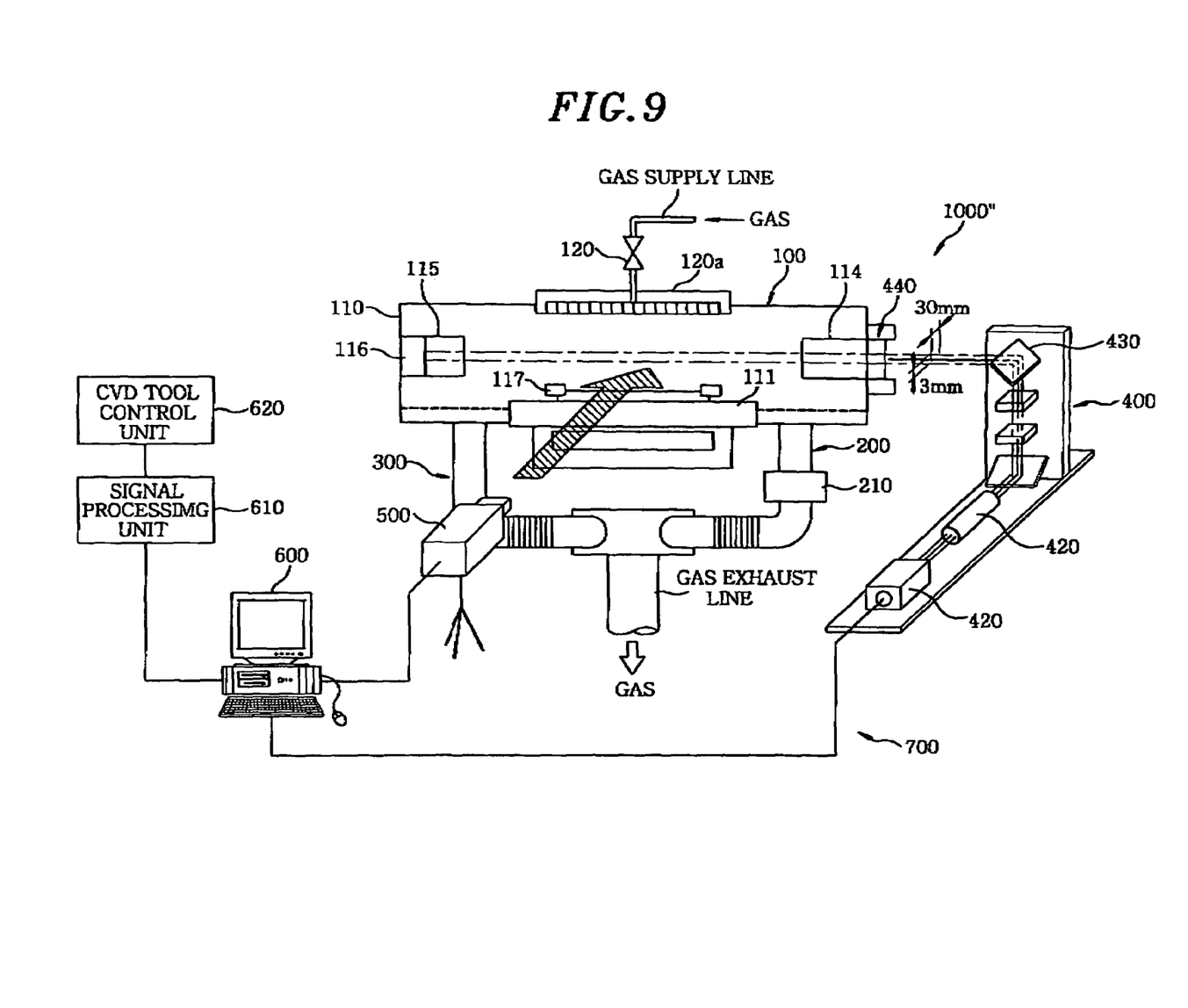
FIG. 9 provides a partial cross sectional view to describe the configuration of the semiconductor manufacturing apparatus shown in FIG. 1 in further detail.

FIG. 9 presents a detailed partial cross sectional view to describe the configuration of the semiconductor manufacturing apparatus 1000 in FIG. 1.

In FIG. 9, a semiconductor manufacturing apparatus 1000" further includes a laser introduction unit 700 in addition to the components shown in FIG. 1. The laser introduction unit 700 has an in situ particle monitoring unit (ISPM) 400 for monitoring particles in a processing chamber 100 at a location; and a charge coupled device (CCD) camera 500 for capturing the image of, for example, the particles scattering the laser beam. The particle monitoring unit 400 and the CCD camera 500 are connected to the PC 600, and a CVD tool controller 620 is connected to the PC 600 via a signal processing unit 610.

The particle monitoring unit 400 has a laser beam source 410 for irradiating a YAG laser beam of a preset wavelength of, for example, 532 nm at an output of 2.5 kW and a pulse of 10 kHz; an optical system 420 for forming the laser beam in a desired shape; a mirror 430 for reflecting the laser beam incident thereon after passing through the optical system 420 in a direction toward the processing chamber 100; and a window member 440 through which the laser is introduced, the window member 440 being provided at a chamber wall 110 of the processing chamber 100. The window member 440 has the same configuration as that of the window member 219 for particle monitoring shown in FIG. 8 and is made of the same material as that of the window member 219. The laser beam reflected by the mirror 430 is guided into the processing chamber 400 through the window member 440 for laser introduction. The beam introduced into the processing chamber 100 is incident on a beam damper 116 via slits 114 and 115.

Further, the CCD camera 500 photographs laser beams scattered by particles within the processing chamber 100 through a window member (not shown) for the CCD camera provided at the chamber wall 110 of the processing chamber 100, and then inputs thus obtained image into the PC 600. Thus, the CCD camera 500 can function as a sensor for counting the number of the laser beams scattered by the particles within the processing chamber 100, while measuring the pulse number of the laser beams. The window member for the CCD camera is formed of the same material as that of the window member 219' for particle monitoring shown in FIG. 8 and has the same configuration. For example, its surface treatment layer is formed of calcium fluoride, so that the erosion of its surface is suppressed and thus the frequency of the window member's replacement can be reduced. Further, reduction in the sensitivity of the sensor can be prevented. Furthermore, a photomultiplier tube can be used instead of the CCD camera 500 as long as it functions as a sensor.

Moreover, the semiconductor manufacturing apparatus 1000" has a focus ring 117 disposed on a wafer stage 111, wherein the focus ring 117 is formed of the same material as that of the window member 219' for particle monitoring shown in FIG. 8 and has the same configuration. Therefore, erosion of the focus ring 117 can be prevented, while achieving insulation, and thus the frequency of its replacement can be reduced.

Referring to FIG. 9, since the components within the processing chamber 100 including the window member 440 for laser introduction, the window member for CCD camera, the focus ring 117 and the like are formed of the same material as that of the window member 219' shown in FIG. 8 and have the same configurations, erosion of their surfaces can be suppressed, enabling reduction of the frequency of their replacement. In addition, due to the prevention of erosion of their surfaces, wafer contamination can be suppressed in the processing chamber 100.

The vacuum apparatus, and the particle monitoring method and program in accordance with the present invention is not limited to the processing chamber or the load lock chamber of the semiconductor manufacturing apparatus, but may be applied to any vessel that defines an evacuable space, for example, a manufacturing apparatus for fabricating a liquid crystal such as a flat panel display and other substrate processing apparatuses.

Moreover, the window members for particle monitoring in accordance with the preferred embodiments of the present invention may be used as a transparent window member disposed between a housing that defines an evacuable space and a particle monitoring unit for monitoring particles within the housing.

While the invention has been shown and described with respect to the preferred embodiments, it will be understood by those skilled in the art that various changes and modifications may be made without departing from the spirit and scope of the invention as defined in the following claims.

What is claimed is:

1. A vacuum apparatus comprising:
   a vessel for defining a predetermined space;
   a gas exhaust unit for exhausting a gas from the vessel via a gas exhaust line;
   at least one gas exhaust control unit installed on the gas exhaust line, for controlling a flow rate of the gas exhausted from the vessel;
   a particle monitoring unit installed on the gas exhaust line between said at least one gas exhaust control unit and the gas exhaust unit, for monitoring particles within the gas exhaust line; and
   a power supply unit for generating an electric discharge within the vessel,
   wherein the power supply unit starts the electric discharge when said at least one gas exhaust control unit permits the exhaust of the gas, and the particles monitored by the particle monitoring unit include the particles detached from the vessel due to the electric discharge.

2. The apparatus of claim 1, wherein the power supply unit generates an electromagnetic stress in the vessel due to the electric discharge.

3. The apparatus of claim 1, further comprising:
   a purge unit for supplying a purge gas into the vessel via a gas supply line; and
   a gas supply control unit installed on the gas supply line between the purge unit and the vessel, for controlling a flow rate of the purge gas supplied into the vessel,
   wherein the gas supply control unit starts a supply of the purge gas when said at least one gas exhaust control unit permits an exhaust of the gas, and the particles monitored by the particle monitoring unit include the particles detached from the vessel due to the supply of the purge gas.

4. A particle monitoring method of a vacuum apparatus having a vessel for defining a predetermined space, comprising the steps of:
   (a) exhausting a gas from the vessel via a gas exhaust line;
   (b) controlling a flow rate of the gas exhausted from the vessel;
   (c) monitoring particles within the gas exhaust line; and
   (d) generating an electric discharge within the vessel,
   wherein the electric discharge is started when the exhaust of the gas is permitted in the step (b), and the monitored particles include the particles detached from the vessel due to the electric discharge.

5. The method of claim 4, wherein an electromagnetic stress is generated due to the electric discharge in the step (d).

6. The method of claim 4, further comprising:
   (e) supplying a purge gas into the vessel via a gas supply line; and
   (f) controlling a flow rate of the purge gas supplied into the vessel,
   wherein, in the step (f), a supply of the purge gas is started when an exhaust of the gas is permitted in the step (b), and the monitored particles include the particles detached from the vessel due to the supply of the purge gas.

7. A computer-executable program, stored in a storage medium, for performing a particle monitoring method of a vacuum apparatus having a vessel for defining a predetermined space, comprising:
   a gas exhaust module for exhausting a gas from the vessel via a gas exhaust line;
   a gas exhaust control module for controlling a flow rate of the gas exhausted from the vessel;
   a particle monitoring module for monitoring particles within the gas exhaust line; and
   an electric discharge module for generating an electric discharge within the vessel,
   wherein the electric discharge module starts the electric discharge when the gas exhaust control module permits the exhaust of the gas, and the particles monitored by the particle monitoring module include the particles detached from the vessel due to the electric discharge.

8. A computer-readable storage medium which stores therein a program, the program comprising:
   a gas exhaust module for exhausting a gas from the vessel via a gas exhaust line;
   a gas exhaust control module for controlling a flow rate of the gas exhausted from the vessel;
   a particle monitoring module for monitoring particles within the gas exhaust line; and
   an electric discharge module for generating an electric discharge within the vessel, wherein the electric discharge module starts the electric discharge when the gas exhaust control module permits the exhaust of the gas, and the particles monitored by the particle monitoring module include the particles detached from the vessel due to the electric discharge.

* * * * *